US008703798B2

(12) United States Patent
Ablordeppey

(10) Patent No.: US 8,703,798 B2
(45) Date of Patent: Apr. 22, 2014

(54) ANTIFUNGAL AND ANTIPARASITIC INDOLOQUINOLINE DERIVATIVES

(75) Inventor: Seth Y. Ablordeppey, Tallahasse, FL (US)

(73) Assignee: Florida A&M University, Tallahassee, FL (US)

( * ) Notice: Subject to any disclaimer, the term of this patent is extended or adjusted under 35 U.S.C. 154(b) by 95 days.

(21) Appl. No.: 13/404,307

(22) Filed: Feb. 24, 2012

(65) Prior Publication Data

US 2012/0157493 A1 Jun. 21, 2012

Related U.S. Application Data

(62) Division of application No. 11/394,158, filed on Mar. 31, 2006, now Pat. No. 8,158,646.

(51) Int. Cl.
*A61K 31/47* (2006.01)
*C07D 215/38* (2006.01)

(52) U.S. Cl.
USPC ............ 514/313; 546/160; 546/153; 514/312

(58) Field of Classification Search
USPC .......................... 514/313, 312; 546/160, 153
See application file for complete search history.

(56) References Cited

U.S. PATENT DOCUMENTS 8,288,410 B2 * 10/2012 Ablordeppey ................ 514/312

OTHER PUBLICATIONS

Dwuma-Badu, D.; Ayim, 1. S.; Fiagbe, N. 1.; Knapp, 1. E.; Schiff P. L.; Jr, Slatkin D. J. *J. Pharm. Sci.* 1978,67,433-434.
Ablordeppey, S. Y.; Hufford, C. D.; Borne, R. F.; Dwuma-Badu, D. *Planta Med.* 1990, 56, 416.
Cimanga K.; De Bruyne T.; Lasure A; Van Pod, B.; Pieters, L.; Claeys, M.; Vanden Berghe, D.; Kambu, K.; Tona, L.; Vlietinck, A 1. *Planta Medica*, 1996, 62,22-27.
Ablordeppey, S. Y.; Fan, P.; Ablordeppey, 1. H.; Mardenborough, L. *Curr Med. Chem.* 1999, 6, 1151-1195].
Oyekan, A O.; Ablordeppey, S. Y *Gen. Pharmacol.* 1993, 24, 1285-1290.
Oyekan, A O.; Ablordeppey, S. Y *Gen. Pharmacol.,* 1993,24,461-469.
Oyekan AO.; Ablordeppey S. *Y Med. Chem. Res.* 1996, 6, 602-610.
Singh, M.; Singh, M. P.; Ablordeppey, S. *Drug Dev Ind Pharm* 1996, 22,377-381].
Noamesi, B. K.; Bamgbose, S. O. A. *Planta Med* 1980,39,51-56].
Bierer D. E.; Fort D. M.; Mendez C. D.; Luo 1.; Imbach P. A; Dubenko L. G.; Jolad S. D.; Gerber, R. E.; Litvak, 1.; Lu Q.; Zhang P.; Reed M. 1.; Waldeck N.; Bruening R. C.; Noamesi B. K.; Hector R. F.; Carlson T. J.; King S. R. *J Med Chem.* 1998,41,894-901.
Boakye-Yiadom, K.; Heman-Ackah, S. M. *J Pharm Sci* 1979, 68,1510-1514. Sawer, 1. K.; Berry M. 1.; Brown M. W.; Ford, J. L. *J Applied Bacteriol*, 1995, 79,314-321.
Dassonneville, L.; Lansiaux, A; Wattelet, A; Wattez, N.; Mahieu, C.; Van Miert, S.; Pieters L.; Bailly, C. *Eur J Pharmacol 2000*, 409, 9-18.
Cimanga, Kanyanga; De Bruyne, Tess; Pieters, Luc; Vlietinck, Arnold J.; Turger, Caesar A. *J Nat Prod* 1997, 60, 688-691.
Wright, C. W.; Phillipson, J. D.; Awe, S. 0.; Kirby, G. c.; Warhurst, D. C.; Quetin-Leclercq, J.; Angenot, L. *Phytother Res* 1996,10, 361-363.
Grellier, P.; Ramiaramanana, L.; Millerioux, V.; Deharo, E.; Schrevel, J.; Frappier, F.; Trigalo, F.; Bodo, B.; Pousset, J.-L. *Phytother Res*, 1996, 10, 317-321.
Kirby, G. C.; Paine, A; Warhurst, D. C.; Noamesi, B. K; Phillipson, J. D. *Phytother Res*, 1995, 9,359-63.
Lisgarten, J. N.; Pous, J.; Coll, M.; Wright, C. W.; Aymami, J. Acta Crystallogr D Biol Crystallogr, 2002, D58, 312-313.
Dassonneville L.; Bonjean K; De Pauw-Gillet, M.-C.; Colson P.; Houssier, C.; QuetinLeclercq, 1; Angenot, L.; Bailly, C. *Biochemistry*, 1999, 38, 7719-26.
Bailly, C.; Laine, W.; Baldeyrou, B.; De Pauw-Gillet, M.-C.; Colson, P.; Houssier, C.; Cimanga, K; Van Miert, S.; Vlietinck, AJ.; Pieters, L. *Anticancer Drug Des*, 2000, 15, 191-201.
Bonj ean, K.; De PauwGillet, M.-C.; Defresne, P.; Colson P.; Houssier, c.; Dassonneville L.; Bailly, C.; Greimers, R.; Wright, c.; Quetin-Leclercq, J.; Tits, M.; Angenot, L. *Biochemistry*, 1998, 37, 5236-5146.
Dassonneville, L.; Lansiaux, A; Wattelet, A; Wattez, N.; Mahieu, c.; Van Miert, S.; Pieters L.; Bailly, C. *Eur J Pharmacol,* 2000, 409, 9-18.
Guyen, B.; Schultes, C. M; Hazel, P.; Mann, J.; Neidle, S. *Org Biomol Chem,* 2004, 2, 981-8.
Ablordeppey, S.Y.; Fan, P.; Clark, A. M.; Nimrod, *A Bioorg Med Chem,* 1999, 7, 343-349.
Mardenborough L. G.; Fan, P. c.; Ablordeppey, S. Y.; Nimrod, A; Clark A M. *Med Chem Res,* 1999,9, 118 -132. c) Oyekan, A. O.; Ablordeppey, S. Y. *Med Chem Res* 1996, 6,602-610.
Ablordeppey, S.Y.; Fan, P.; Li, S.; Clark, A M.; Hufford, C. D. *Bioorg Med Chem,* 2002, 10,1337-1346.
Holt, S. J.; Petrow, V. *.J Chem. Soc.* 1947,607-611.
Fan, P.; Ablordeppey, S. Y. *J Heterocycl Chem,* 1997,34, 1789-1794.
Radl, S; Konvicka, P.; Vachal, P. *J Heterocycl Chem,* 2000, 37, 855-862.
Yang, S.-W.; Abdel-Kader, M.; Malone, S.; Werkhoven, M. C. M.; Wisse, J. H.; Bursuker, I.; Neddermann, K; Fairchild, C.; Raventos-Suarez, C.; Menendez, AT.; Lane, K.; Kingston, D. G. I. *J Nat Prod,* 1999, 62, 976-983.
Bierer D. E.; Dubenko L. G.; Zhang P.; Lu Q.; Imbach P. A; Garofalo A W.; Phuan P. -W.; Fort D. M.; Litvak J.; Gerber R. E.; Sloan B.; Luo J.; Cooper R.; Reaven G. M. *J Med Chem* 1998, 41, 2754-2764.

(Continued)

*Primary Examiner* — Charanjit Aulakh
(74) *Attorney, Agent, or Firm* — Thomas|Horstemeyer, LLP

(57) ABSTRACT

An indoloquinoline wherein the quarternary N-5 atom is a straight C(1-5) chain, a branched C(1-5) chain, a heteroatom chain, a straight chain substituted terminally by a cycloalkyl or aromatic ring, a branched chain substituted terminally by a cycloalkyl or aromatic ring, a heteroatom chain substituted terminally by a cycloalkyl or aromatic ring; the 10 position is N—$R_{10}$, O, S, S=O, $CH_2$, or C=O, where $R_{10}$ is a branched C(1-5) chain, a heteroatom chain, a straight chain substituted terminally by a cycloalkyl or aromatic ring, a branched chain substituted terminally by a cycloalkyl or aromatic ring, a heteroatom chain substituted terminally by a cycloalkyl or aromatic ring. In one embodiment the quarternary N-5 atom is —$CH_3$ and the 10 position is N—$(CH_2)_5$-Ph.

9 Claims, No Drawings

(56) References Cited

OTHER PUBLICATIONS

Chen, J. J.; Deady, L. W.; Desneves, 1.; Kaye, A. J.; Finlay, G. J.; Baguley, B. C.; Denny, W. A. *Bioorg Med Chem*, 2000, 8, 2461-2466.

Cooper, M. M.; Lovell, 1. M.; Joule, J. A. *Tetrahedron Leu*, 1996, 37, 4283-4286.

Guoyi, M.; Khan, S.; Jacob, M. R; Tekwani, B. L.; Li, Z.; Pasco, D. S.; Walker, L. A.; Khan, 1. A.; *Antimicrob Agents Chemother*, 2004, 48, 4450-4452.

Franzblau et al [1998. *J Clin Microbiol*, 36, 362-366].

Muhammad, 1.; Bedir, E.; Khan, S. I.; Tekwani, B. L.; Khan, I. A.; Takamatsu, S.; Pelletier, 1.; Walker, L. A. *J Nat Prod.* 2004, 67, 772-7.

Muhammad, 1.; Dunbar, D. C.; Khan, S. 1.; Tekwani, B. L.; Bedir, E.; Takamatsu, S.; Ferreira, D, Walker LA., *J Nat Prod.* 2003, 66, 962-7].

* cited by examiner

ANTIFUNGAL AND ANTIPARASITIC INDOLOQUINOLINE DERIVATIVES

This application is a Divisional of U.S. patent application entitled "Antifungal and Antiparasitic Indoloquinoline Derivatives" filed on Mar. 31, 2006 and assigned Ser. No. 11/394,158.

BACKGROUND OF THE INVENTION

The tetracyclic structure of indolo[3,2-b]quinolines, also referred to as quindoline (1) constitutes an important structural moiety in the literature because of its effect on numerous biological functions [a) Dwuma-Badu, D.; Ayim, 1. S.; Fiagbe, N. 1.; Knapp, 1. E.; Schiff P. L.; Jr, Slatkin D. J. *J. Pharm. Sci.* 1978, 67, 433-434. b) Ablordeppey, S. Y.; Hufford, C. D.; Borne, R. F.; Dwuma-Badu, D. *Planta Med.* 1990, 56, 416. c) Cimanga K.; De Bruyne T.; Lasure A; Van Poel, B.; Pieters, L.; Claeys, M.; Vanden Berghe, D.; Kambu, K.; Tona, L.; Vlietinck, A 1. *Planta Medica,* 1996, 62, 22-27. d) Ablordeppey, S. Y.; Fan, P.; Ablordeppey, 1. H.; Mardenborough, L. *Curr Med. Chem.* 1999, 6, 1151-1195]. For example, cryptolepine (2a & b) and several of its analogs display anti-aggregatory [a) Oyekan, A O.; Ablordeppey, S. Y *Gen. Pharmacol.* 1993, 24, 1285-1290. b) Oyekan, A O.; Ablordeppey, S. Y *Gen. Pharmacol.,* 1993, 24, 461-469. c) Oyekan A O.; Ablordeppey S. Y *Med. Chem. Res.* 1996, 6, 602-610. d) Singh, M.; Singh, M. P.; Ablordeppey, S. *Drug Dev Ind Pharm* 1996, 22, 377-381], antihypertensive [Noamesi, B. K.; Bamgbose, S. O. A. *Planta Med* 1980, 39, 51-56], antihyperglycemic [Bierer D. E.; Fort D. M.; Mendez C. D.; Luo 1.; Imbach P. A; Dubenko L. G.; Jolad S. D.; Gerber, R. E.; Litvak, 1.; Lu Q.; Zhang P.; Reed M. 1.; Waldeck N.; Bruening R. C.; Noamesi B. K.; Hector R. F.; Carlson T. J.; King S. R. J *Med Chem.* 1998, 41, 894-901], antibacterial [Boakye-Yiadom, K.; Heman-Ackah, S. M. *J Pharm Sci* 1979, 68, 1510-1514. Sawer, 1. K.; Berry M. 1.; Brown M. W.; Ford, J. L. *J Applied Bacteriol,* 1995, 79, 314-321], anticancer [Dassonneville, L.; Lansiaux, A; Wattelet, A; Wattez, N.; Mahieu, C.; Van Miert, S.; Pieters L.; Bailly, C. *Eur J Pharmacol* 2000, 409, 9-18], antimalarial [a) Cimanga, Kanyanga; De Bruyne, Tess; Pieters, Luc; Vlietinck, Arnold J.; Turger, Caesar A. *J Nat Prod* 1997, 60, 688-691. b) Wright, C. W.; Phillipson, J. D.; Awe, S. 0.; Kirby, G. c.; Warhurst, D. C.; QuetinLeclercq, J.; Angenot, L. *Phytother Res* 1996, 10, 361-363. c) Grellier, P.; Ramiaramanana, L.; Millerioux, V.; Deharo, E.; Schrevel, J.; Frappier, F.; Trigalo, F.; Bodo, B.; Pousset, J.-L. *Phytother Res,* 1996, 10, 317-321. d) Kirby, G. C.; Paine, A; Warhurst, D. C.; Noamesi, B. K; Phillipson, J. D. *Phytother Res,* 1995, 9, 359-63], activities among others.

A unified mechanism by which the drug produces the different biological activities has not been elucidated. However, cryptolepine has been shown to bind to DNA fragments [Lisgarten, J. N.; Pous, J.; Coll, M.; Wright, C. W.; Aymami, J. Acta Crystallogr D Biol Crystallogr, 2002, D58, 312-313] in a rather unique fashion. Furthermore, it intercalates DNA and stimulates topoisomerase II mediated cutting of DNA [a) Dassonneville L.; Bonjean K; De Pauw-Gillet, M.-C.; Colson P.; Houssier, C.; QuetinLeclercq, 1; Angenot, L.; Bailly, C. *Biochemistry,* 1999, 38, 7719-26. b) Bailly, C.; Laine, W.; Baldeyrou, B.; De Pauw-Gillet, M.-C.; Colson, P.; Houssier, C.; Cimanga, K; Van Miert, S.; Vlietinck, A J.; Pieters, L. *Anticancer Drug Des,* 2000, 15, 191-201. c) Bonjean, K.; De PauwGillet, M.-C.; Defresne, P.; Colson P.; Houssier, c.; Dassonneville L.; Bailly, C.; Greimers, R.; Wright, c.; Quetin-Leclercq, J.; Tits, M.; Angenot, L. *Biochemistry,* 1998, 37, 5236-5146. d) Dassonneville, L.; Lansiaux, A; Wattelet, A; Wattez, N.; Mahieu, c.; Van Miert, S.; Pieters L.; Bailly, C. *Eur J Pharmacol,* 2000, 409, 9-18]. More recently, cryptolepine has been identified as a potential inhibitor of telomerase and a G-quadruplex DNA stabilizing agent [Guyen, B.; Schultes, C. M; Hazel, P.; Mann, J.; Neidle, S. *Org Biomol Chem,* 2004, 2, 981-8].

The structures of quindoline and its basic and salt forms are:

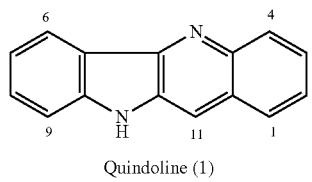

Quindoline (1)

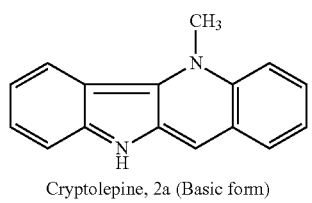

Cryptolepine, 2a (Basic form)

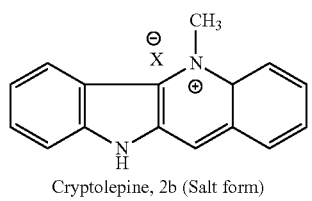

Cryptolepine, 2b (Salt form)

It has been shown that alkylation of the N-5 atom in quindoline is necessary for several of the therapeutic activities associated therewith [a) Ablordeppey, S. Y.; Fan, P.; Clark, A. M.; Nimrod, A *Bioorg Med Chem,* 1999, 7, 343-349. b) Mardenborough L. G.; Fan, P. c.; Ablordeppey, S.Y.; Nimrod, A; Clark A M. *Med Chem Res,* 1999, 9, 118-132. c) Oyekan, A. O.; Ablordeppey, S. Y. *Med Chem Res* 1996, 6, 602-610]. In particular, it has been reported that co-phenylpentyl and co-cyclohexylpentyl moieties on the N-5 atom of the quindoline ring produce a high antifungal potency and broadens the spectrum of activities. It is interesting to note that N-5 alkylation produces an anhydronium base in which the N-5 nitrogen becomes positively charged, i.e., aromatic quaternary nitrogen (2b), under acidic conditions but reverts to $S_p3$ type nitrogen under basic conditions (2a). This physical characteristic of cryptolepine is also accompanied by a color change from pink in a basic medium to orange in an acidic environment. This unique behavior may allow for easy entry into cells in the basic form, despite its quaternary nature, and yet produce its pharmacological effect in the salt form.

It is an object of the present invention to provide novel quindoline compounds having one or more of a variety of therapeutic properties.

SUMMARY OF THE INVENTION

The above and other objects are realized by the present invention, one embodiment of which relates to compounds having the formula:

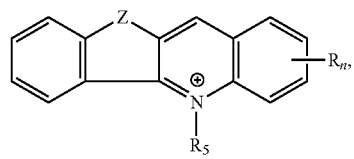
[I]

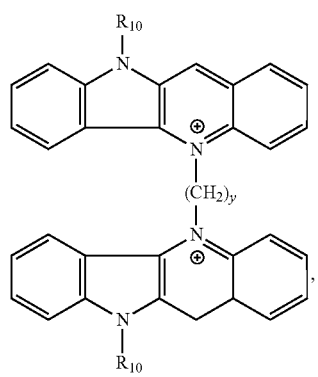
[II]

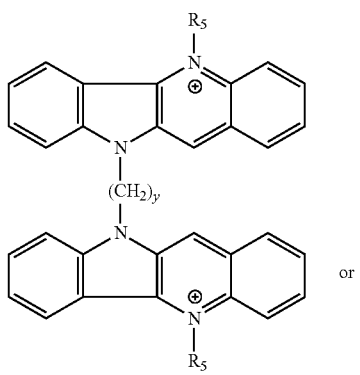
[III]

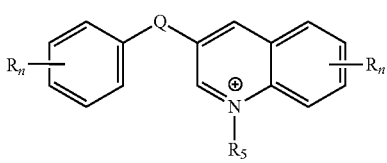
[IV]

wherein: R is an electron withdrawing or electron donating moiety;

$R_5$ and $R_{10}$ may be the same or different and are a straight or branched 1-5 carbon or heteroatom chain substituted terminally by a cycloalkyl or aromatic ring, or other structural isomer or complex thereof;

n is the position of substitution of R;

Z is N—$R_{10}$, O, S, S=O, $CH_2$ or C=O;

y is 1-5 and

Q is Z or NH, with the proviso that, where Z is NH, N—$CH_3$, S or O and $R_n$ is H, $R_5$ may not be $CH_3$.

Another embodiment of the invention relates to quaternary salts of the above compounds having the formula:

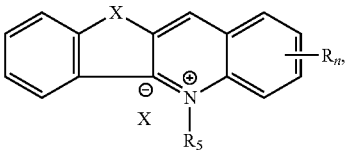
[V]

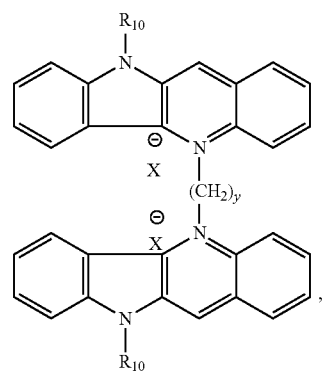
[VI]

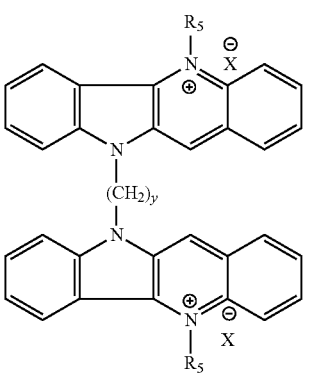
[VII]

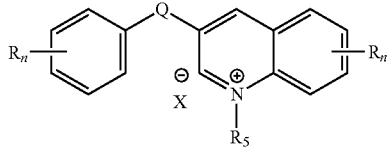
[VIII]

wherein: x is an anion.

A still further embodiment of the invention concerns pharmaceutical composition comprising a pharmacologically effective amount of a compound having one of the above formulas and a pharmaceutically acceptable carrier therefore.

An additional embodiment of the invention relates to a method of treating a mammal in need of therapy comprising administering thereto a pharmacologically effective amount of a compound having one of the above formulas.

DETAILED DESCRIPTION OF THE INVENTION

The present invention is predicated on the discovery that the substitution of certain groups at certain locations on the quindoline group produces compounds having a wide variety of pharmacological utilities, e.g., antiinfective, antileishmanial, antimycobacterial, antimalarial, antituberculosis or anticancer.

To test the hypothesis that a charged N-5 atom is necessary for producing biological activity in the quindoline moiety, the N-10 atom was alkylated (see Chart I) to prevent an anhydronium base formation and to produce a compound with a permanently charged N-5 atom (3a). Because compound 3a showed antifungal activity, it was previously reported that the active form of the indoloquinoline ring system is the salt form in which N-5 is positively charged [Ablordeppey, S. Y.; Fan, P.; Li, S.; Clark, A M.; Hufford, C. D. *Bioorg Med Chem*, 2002, 10, 1337-1346]. This view is consistent with the binding mode of cryptolepine to DNA fragments reported by Aymami et al [Lisgarten, J. N.; Pous, J.; Coll, M.; Wright, C. W.; Aymami, J. *Acta Crystallogr D Biol Crystallogr*, 2002, D58, 312-313] on the basis of x-ray crystallographic work.

Chart 1: Compounds synthesized and tested for biological activity

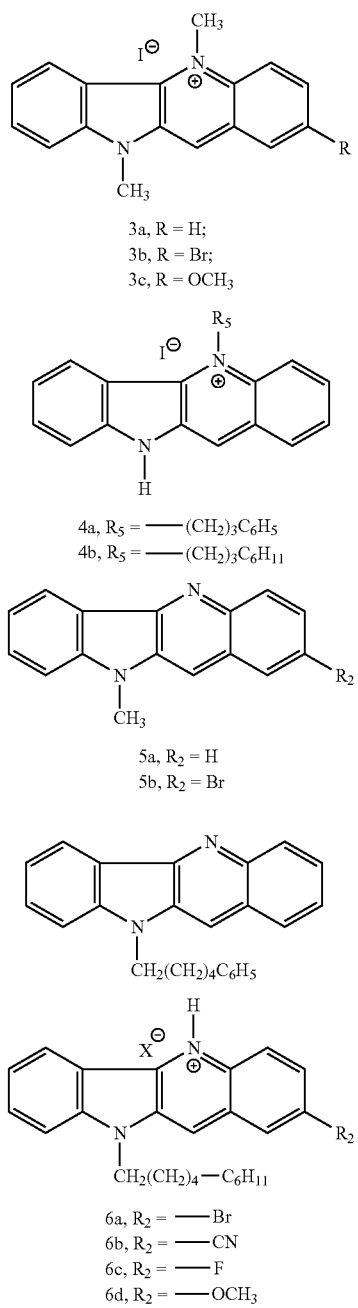

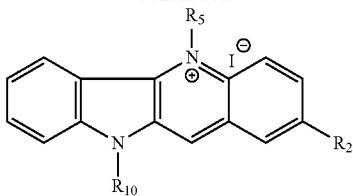

7a, $R_2$ = H; $R_5$ = $CH_3$; $R_{10}$ = —$(CH_2)_5$—Ph
7b, $R_2$ = H; $R_5$ = —$(CH_2)_5$—Ph; $R_{10}$ = $CH_3$
7c, $R_2$ = Br; $R_5$ = —$(CH_2)_5$—Ph; $R_{10}$ = $CH_3$

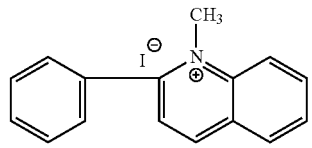

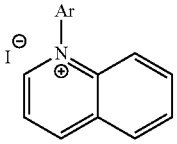

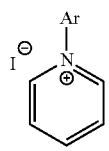

Ar = ω-phenyllpentyl-

Thus, it was decided to investigate the effect of various combinations of substituents, on the N-5 and N-10 atoms, as well as other portions of the molecule, including bis-quindolines, on the pharmacological properties of these compounds.

The construction of the tetracyclic structure of quindoline has been widely reported [a) Holt, S. J.; Petrow, V. *J. Chem. Soc.* 1947, 607-611. b) Fan, P.; Ablordeppey, S. Y. *J Heterocycl Chem,* 1997, 34, 1789-1794. c) Radl, S; Konvicka, P.; Vachal, P. *J Heterocycl Chem,* 2000, 37, 855-862. d) Yang, S.-W.; Abdel-Kader, M.; Malone, S.; Werkhoven, M. C. M.; Wisse, J. H.; Bursuker, I.; Neddermann, K; Fairchild, C.; Raventos-Suarez, C.; Menendez, A T.; Lane, K.; Kingston, D. G. I. *J Nat Prod,* 1999, 62, 976-983. e) Bierer D. E.; Dubenko L. G.; Zhang P.; Lu Q.; Imbach P. A; Garofalo A W.; Phuan P.-W.; Fort D. M.; Litvak J.; Gerber R. E.; Sloan B.; Luo J.; Cooper R.; Reaven G. M. *J Med Chem* 1998, 41, 2754-2764. f) Chen, J. J.; Deady, L. W.; Desneves, 1.; Kaye, A. J.; Finlay, G. J.; Baguley, B. C.; Denny, W. A. *Bioorg Med Chem,* 2000, 8, 2461-2466. g) Cooper, M. M.; Lovell, 1. M.; Joule, J. A. *Tetrahedron Lett,* 1996, 37, 4283-4286].

Herein a previously reported method [Holt, et al, supra] was employed to construct the quindoline unit. A substituted or unsubstituted anthranilic acid was acylated with 2-bromoacetyl bromide and the resulting alkyl halide was used in alkylating aniline. The alkylated aniline in the presence of polyphosphoric acid (PP A) underwent a double cyclization reaction to yield a quindolone which was chlorinated with phosphorus oxychloride (POCl). The resulting chloride was dechlorinated with hydrogen on palladium to obtain the desired quindoline. (Scheme 1).

Scheme 1: The general synthetic method for substituted quindolines.

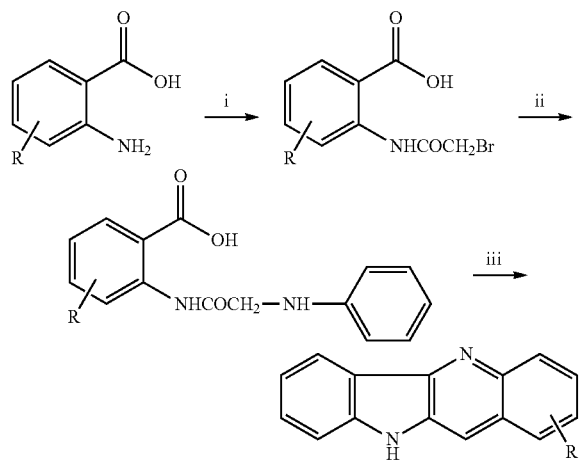

Reagents: i) BrCH₂COBr₂, NaOH; ii) DMF, PhNH₂; iii) a) PPA, 130°; b) POCl₃; c) H₂/10% Pd—C Specifically alkylating either the N-5 or N-10 atoms was accomplished using methods previously reported [Fan et al, supra]. However, the synthesis of the bis-quindolines, where they were joined on the N-5 atoms was accomplished by heating quindoline with 1,4-diiodobutane (9) or the corresponding 1,5-diiodopentane (10). The formation of bis-quindolines, where the N-10 atoms were joined together required a strongly basic medium and was achieved by the introduction of sodamide and the subsequent alkylation was accomplished in a similar manner (Scheme 2).

Scheme 2: Synthesis of bis-quindolines

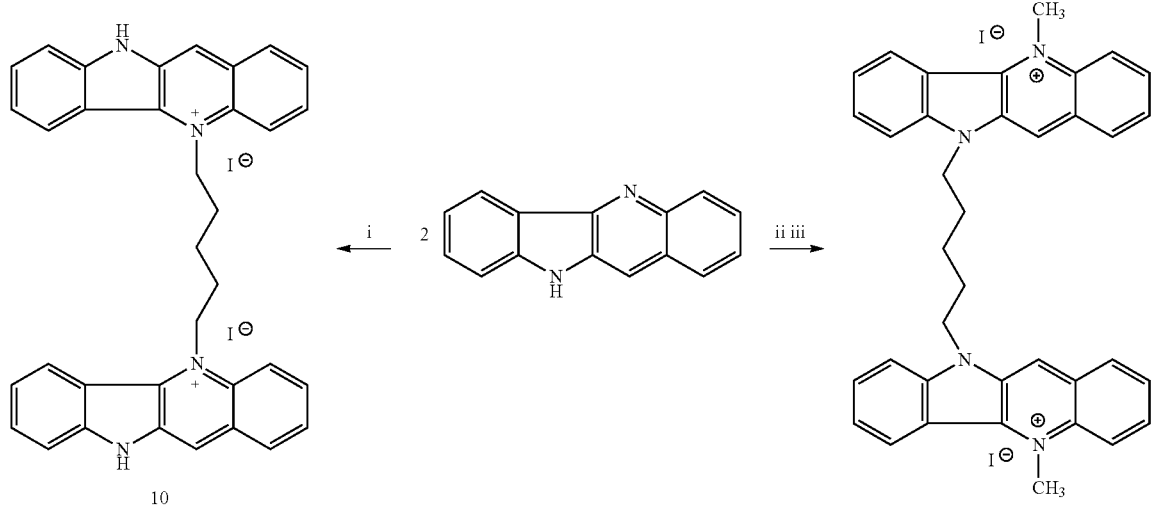

Reagents: i) Trimethylene sulfone, I(CH₂)₅I; ii) NaH, I(CH₂)₅I; iii) CH₃I, TMS.

Compounds were evaluated in vitro against a panel of microorganisms, including *Candida albicans* ATCC 90028 (Ca), *C. krusei* ATCC 6258 (Ck), *Cryptococcus neoformans* ATCC 90113 (Cn), *Staphylococcus aureus* ATCC 29213 (Sa), methicillin-resistant *S. aureus* ATCC 43300 (MRSA), *Pseudomonas aeruginosa* ATCC 27853 (Pa), *Aspergillus fumigatus* ATCC 90906 (Aj), and *Mycobacterium intracellulare* ATCC 23068 (Mi) as previously reported [Guoyi, M.; Khan, S.; Jacob, M. R; Tekwani, B. L.; Li, Z.; Pasco, D. S.; Walker, L. A.; Khan, 1. A.; *Antimicrob Agents Chemother,* 2004, 48, 4450-4452]. All organisms were obtained from the American Type Culture Collection (Manassas, Va.). Susceptibility testing was performed using a modified version of the NCCLS methods [a) National Committee for Clinical Laboratory Standards. 2000. Methods for dilution antimicrobial susceptibility tests for bacteria that grow aerobically. M7-A5. National Committee for Clinical Laboratory Standards, Wayne, Pa. b) National Committee for Clinical Laboratory Standards, 1997, Reference method for broth dilution antifungal susceptibility testing of yeasts. Approved standard M27-A. National Committee for Clinical Laboratory Standards, Wayne, Pa. c) National Committee for Clinical Laboratory Standards. 2000. Susceptibility testing of mycobacteria, nocardia, and other aerobic actinomycetes, 2nd ed. Tentative standard M24-T2. National Committee for Clinical Laboratory Standards, Wayne, Pa.] for all organisms except for *M. intracellulare*, for which the modified Alamar blue procedure described by Franzblau et al [1998. *J Clin Microbiol*, 36, 362-366] was followed. Briefly, samples (dissolved in DMSO) were serially diluted by using 0.9% saline and transferred in duplicate to 96-well microplates. Microbial inocula were prepared after comparison of the absorbance (at 630 nm) of cell suspensions to the 0.5 McFarland standard and dilution of the suspensions in broth (Sabouraud dextrose and cation-adjusted Mueller-Hinton broth [Difco] for the fungi and bacteria, respectively, and 5% Alamar blue [BioSource international] in Middlebrook 7H9 broth with oleic acid-albumin-dextrose-catalase enrichment for *M. intracellulare*) to afford recommended inoculum sizes. Microbial inocula were added to the samples to achieve a final volume of 200 μl and final sample concentrations starting with 100 μg/ml. Growth, solvent, and medium controls were included on each test plate. The plates were read at either 630 nm or excitation and emission wavelengths of 544 and 590 nm (for Mi) prior to and after incubation. Percent growth was calculated and plotted with the concentration tested to afford the concentration that inhibits 50% of growth (IC50). Antimalarial and cytotoxicity testing were conducted in a similar manner as previously reported [a) Muhammad, 1.; Bedir, E.; Khan, S. I.; Tekwani, B. L.; Khan, I. A.; Takamatsu, S.; Pelletier, 1.; Walker, L. A. *J Nat Prod.* 2004, 67, 772-7. b) Muhammad, 1.; Dunbar, D. C.; Khan, S. 1.; Tekwani, B. L.; Bedir, E.; Takamatsu, S.; Ferreira, D, Walker L A., *J Nat Prod.* 2003, 66, 962-7].

The results were as follows. Re-evaluation of N-I0 methylated cryptolepines (3a-3c), confirmed that substitution at the 2-position with bromine, an electron withdrawing group while enhancing anticryptococcal activity, had no effect on anticandida action. On the other hand, the electron-donating methoxy group has little or no effect on both activities when compared to 3a. It had previously been shown that alkylation of the N-5 in quindoline with ω-phenylpentyl or ω-cyclohexylpentyl moiety as in 4a and 4b enhances antifungal activity (Table 1). In this form, the positively charged N5 atom is retained. Thus, it became of interest to investigate the contribution of the positively charged N5 atom.

while the active protonated form interferes with cell reproduction. The results confirm that N-I0 alkylated analogs of quindoline have little or no activity as antifungal agents. Since quindoline salts have no antifungal activities, but N-5 alkylated quindolines have activity, it stands to reason that a positive N-5 atom along with a hydrophobic interaction with the N-5 alkyl groups may be important for the actions of these alkylated indoloquinolines.

Since alkylation of N-10 is tolerated and methylation of both N-5 and N-I0 appears to be beneficial (3a-c), it became of interest to examine the position for optimum placement of the alkyl groups. In this regard, compounds 7a-c were prepared and evaluated for their antifungal properties and the results are recorded in Table 1. These results indicate that when N-5 is substituted with the longer ω-phenylpentyl moiety and N-I0 is methylated, this combination appears to be more potent than the reverse. However, there appears to be no significant overall improvement in potency compared to the doubly methylated compounds, 3a-3c.

The importance of the quaternary N-5 atom in these indoloquinolines also led to the investigation of compounds

TABLE 1

Physiochemical data and antifungal activities of synthetic compounds.

| | Recrystallization Solvent | % Yield[a] | MP (° C.)[b] | Empirical[c] Formula | IC50 (μg/ml)[d] Cn | Ca |
|---|---|---|---|---|---|---|
| 2b* | MeOH/Et$_2$O | 73 | 265-268 | C$_{16}$H$_{13}$N$_2$I | 15.6[d] | 0.8-180 |
| 3a* | MeOH/Et$_2$O | 100 | 304-306 | C$_{17}$H$_{15}$N$_2$I | 6.3[d] | 3.1[d] |
| 3b* | MeOH/Et$_2$O | 57 | 285-288 | C$_{17}$H$_{14}$N$_2$BrI | 0.4[d] | 3.1[d] |
| 3c* | MeOH/Et$_2$O | 27 | 262-264 | C$_{18}$H$_{17}$N$_2$OI•1.0MeOH | 4.3 | 2.1 |
| 4a* | MeOH/Et$_2$O | 67 | 218-219 | C$_{25}$H$_{25}$N$_2$Br | 1.3 | 80 |
| 4b* | MeOH/Et$_2$O | 34 | 262-264 | C$_{25}$H$_{31}$N$_2$Br | 0.3 | ≤1.3 |
| 5a | Hexane/EtOAc | 94 | 110-112 | C$_{16}$H$_{12}$N$_2$•0.3H$_2$O | 62.5[d] | 125[d] |
| 5b | Hexane/EtOAc | 62 | 160-162 | C$_{16}$H$_{11}$N$_2$Br | 11 | 43 |
| 5c | MeOH/Et$_2$O | 54 | 223-224 | C$_{26}$H$_{25}$N$_2$Cl•HCl | 9.0 | 18.0 |
| 6a | MeOH/Et$_2$O | 54 | 223-224 | C$_{26}$H$_{29}$N$_2$Br•HCl | >50 | >50 |
| 6b | MeOH/Et$_2$O | 73 | 229-231 | C$_{27}$H$_{29}$N$_3$•HCl | >50 | >50 |
| 6c | MeOH/Et$_2$O | 64 | 231-233 | C$_{26}$H$_{29}$N$_2$F•HCl | >50 | >50 |
| 6d | MeOH/Et$_2$O | 71 | 232-234 | C$_{27}$H$_{32}$N$_2$O•HCl | >50 | >50 |
| 7a | MeOH/Et$_2$O | 67 | 215-217 | C$_{27}$H$_{27}$N$_2$I | 15 | >20 |
| 7b* | MeOH/Et$_2$O | 30 | 203-204 | C$_{27}$H$_{27}$N$_2$Br•1.4MeOH | 4.3 | 4.3 |
| 7c | MeOH/Et$_2$O | 100 | 217-220 | C$_{27}$H$_{25}$N$_2$Br$_2$•0.5H$_2$O•1.0MeOH | 1.3 | 43 |
| 8a | EtOH/Et$_2$O | 22 | 196-198 | C$_{16}$H$_{14}$NI | 43 | 180 |
| 8b | EtOH/Et$_2$O | 65 | 79-83 | C$_{20}$H$_{28}$NBr•0.8H$_2$O | 20 | 80 |
| 8c | MeOH/Et$_2$O | 45 | 86-89 | C$_{16}$H$_{26}$NBr•1.4H$_2$O | >15 | >15 |
| 9 | MeOH/CH$_2$Cl$_2$ | 78 | 252-254 | C$_{34}$H$_{30}$N$_4$I$_2$•0.5H$_2$O | 4.0 | >50 |
| 10 | MeOH/Et$_2$O | 76 | 256-258 | C$_{35}$H$_{30}$N$_4$I$_2$•3.5H$_2$O | 1.5 | >50 |
| 11 | MeOH/Et$_2$O | 87 | — | C$_{35}$H$_{28}$N$_4$•0.6H$_2$O | NA | NA |
| 12 | MeOH/Et$_2$O | 75 | 238-240 | C$_{37}$H$_{34}$N$_4$I$_2$•0.5H$_2$O | 2.0 | 2.0 |
| Amphotericin B | | | | | 0.6 | 0.1 |

One way a non-N-5 alkylated quindoline can produce a positively charged N-5 atom is to form the salt. Hence, two N-I0 methylated analogs in their salt form (5a & 5b) were synthesized for evaluation. The results showed that these compounds were only weakly active against *C. neoformans* and *C. albicans*. Compound 5c was synthesized to explore the possibility that antifungal potency might be enhanced the same way ω-phenylpentyl group enhanced the potency of quindoline. Indeed, a moderate increase in potency (~10-fold) over 5a was observed. However, the enhanced potency of compound 4b over cryptolepine and the increased potency of 2-substituted analogues led to the synthesis of several N-I0 substituted analogs (6a-6d) with the (O-cyclohexylpentyl) moiety. The N10 alkylated analogs were also of interest because N-10 alkylation enables both the free base form and the salt form to co-exist in an aqueous medium, allowing the free base form of the drug to penetrate fungal cell membranes 8a-8c in order to dispel the notion that the antifungal activity of these compounds was intricately associated with any functionality with a quaternary N+ atom and an alkyl function such as the (O-cyclohexylpentyl moiety. As shown in Table 1, there was little antifungal activity associated with 8a-c suggesting that the A and B rings may be important for the activities observed in the quindolines.

As a result of the fact that phenyl and cyclohexyl moieties placed five carbon atoms away from N$^+$-5 display high antifungal potency, it became necessary to investigate the possibility that bisquindolines five carbons from each other might similarly enhance antifungal potency perhaps by interacting with two adjoining DNA molecules. In this regard, compounds 9 and 10 (n=4 and 5 respectively) in which the pyridine nitrogens are connected, and 11 and 12, where the tetracycles are joined by the indole N-atoms were synthesized, and evaluated for biological activity. The results show that the positively charged quaternary atom is required for activity even in the bis-quindolines. However, there was little difference in the antifungal activities of 10 and 12 when compared together and with the mono-quindolines.

A selected number of the compounds (7a, 9, 10 and 12) was further evaluated in additional assays with cryptolepine as the benchmark, to explore their antimicrobial spectrum. Their cytotoxicities to mammalian cells were also determined. The results are reported in Tables 2 and 3. Evaluation of these results show that compounds 7a, 10 and 12 have more expansive antimicrobial/antiparasitic spectra than cryptolepine. All three compounds also display activity against methycillin-resistant *Staphylococcus aureus* (MRSA). Similarly, all four compounds displayed significant activity against *Mycobacterium intracellulare* (Mi). Among the four compounds tested however, only 7a showed significant potency against *Aspergillus fumigatus* (At), *Candida krusei* (Ck) and *Plasmodium falciparum* (Pf) and only compound 10 displayed activity against *Pseudomonas aeruginosa* (Pa). Thus, among the bis-quindolines, joining the pyridine nitrogens (compounds 9 and 10) by an alkyl chain appears to be more effective than through the indole nitrogen (compound 11). In addition, the 5 chain compound (10) was more potent than the 4 chain structure (9). Interestingly, cryptolepine was more potent than any of the four selected compounds against the malaria parasite *P. falciparum* while all four compounds were less cytotoxic to mammalian cells than cryptolepine. It is important to note that these compounds may not be acting through their monomeric units since that would have resulted in similar or higher toxicity and decreased potency per unit weight of compound. The fact that compounds 10 and 12 displayed no cytotoxicity up to 23.8 µg/ml and are potent against a wide spectrum of microorganisms, suggest that these bis-quindolines may have therapeutic advantage over their monomeric counterparts as new antiinfectives.

TABLE 2

The effect of N-alkylation on the antimicrobial activity of selected quindolines

| Compound | Effect on Other Microorganisms Tested (IC50 µg/ml) | | | | | |
|---|---|---|---|---|---|---|
| | Af | Ck | MRSA | Mi | Pa | Sa |
| Cryptolepine | >20 | 4.5 | 20 | 15.0 | NA | NT |
| 7a | 2.5 | 2.0 | 2.0 | 1.0 | NA | NT |
| 9 | >20 | >20 | >20 | 5.5 | NA | NT |
| 10 | 20 | NT | 3.0 | 7.0 | 1.5 | 3.0 |
| 12 | 20 | 15 | 6.0 | 15.0 | NA | NT |
| Amphotericin B | 0.31 | 0.60 | | | NT | NT |
| Ciprofloxacin | | | 0.15 | 0.20 | 0.06 | 0.10 |

Abbreviations in Table 2:
NT = Not Tested.
NA = Not active up to 20 µg/ml.
*Aspergillus fumigatus* (Af), *Candida krusei* (Ck), Methicillin-Resistant *Staphylococcus aureus* (MRS), *Mycobacterium intracellulare* (Mi); *Pseudomonas aeruginosa* (Pa): *Staphylococcus aureus* (Sa),

TABLE 3

Antimalarial activity and Cytotoxicity of selected quindolines

| | Plasmodium falciparum (IC50 ng/ml) | | | | Cytotoxicity (Vero) |
|---|---|---|---|---|---|
| Compound | Pf (D6) | SI | Pf (W2) | SI | (TC$_{50}$ ng/ml) |
| Cryptolepine | 44 | 54 | 130 | 18.5 | 2400 |
| 7a | 62 | 145 | 28 | 321 | 9000 |
| 9 | >528 | | NA | | NC |
| 10 | 1300 | >18.3 | 1000 | >23.8 | >23800 |
| 12 | 260 | >91.5 | 140 | >170 | >23800 |
| Chloroquine | 17.0 | | 75 | | >23800 |
| Artemisinin | 8.5 | | 3.1 | | >23800 |
| Amphotericin B | NT | | NT | | 6500 |

Abbreviations in Table 3:
NC = No cytotoxicity observed up to 5 µg/ml;
NT = Not Tested.
NA = Not active up to 20 µg/ml;
SI = IC50 (vero cells)/IC50 (Pf).
D6 = D6 Clone;
W2 = W2 Clone.

Evaluation of the above indoloquinolines confirms the importance of N-5 alkylation. The basicity of this nitrogen and consequently the formation of the positive charge appear to be important. On the other hand, alkylation of the non-basic indole nitrogen appears not to lead to activity. Despite this observation, it appears that simultaneous alkylation of both nitrogen atoms results in improved potency and extension in the antiinfective spectrum. Similarly, bis-quindolines obtained by double alkylation of the pyridine N-5 atoms produce a broad spectrum antimicrobial activity while connection through the indole N10 atoms led to compounds without activity. Subsequent alkylation of the N5 in this type of bis-quindolines however, resulted in similar antiinfective properties. The broad spectrum of antimicrobial actions and the lower cytotoxicity displayed by the bis-quindolines indicates this group may be acting through a different mechanism of action from that of their monomeric counterpacts.

The active agents identified by the present invention may be employed for the treatment of pathological conditions in the same manner and in approximately the same dosages utilized when employing those quindolines presently known in the art for similar purposes.

There are few efficacious drugs on the market to treat new and emerging opportunistic infections (OIs) such as those associated with HIV/AIDS and other immunocomprised conditions. The present invention identifies certain substituted indoloquinolines, benzothienoquinolines, phenylsulfanylquinolines and their analogs as novel agents against these opportunistic infections.

Synthesis of [Ph$_3$Bi(OAc)$_2$]

To a solution of Ph$_3$Bi (5 g, 11.3 mmol) in 30 ml of dichloromethane/THF (7:3) at 0° C. was added drop wise CH$_3$CO$_3$H (2.9 ml of a 32% solution in CH$_3$COOH, 1.2 eq). The mixture was stirred at room temperature for 1 hr. Et$_2$O (30 ml) was added to form a precipitate which was filtered, washed with Et$_2$O, collected and dried, (mp: 192-194° C.).

The isolated yield was (5.7 g). ¹H NMR (CDCl₃): δ 1.82 (S, 6H), 7.45-7.60 (m, 9H), 8.15 (d, J=8.1 Hz, 6H).

Synthesis of 3-Anilinoquinoline

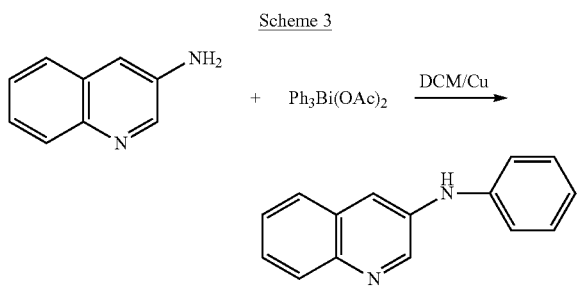

Scheme 3

To a solution of 2-aminoquinoline (800 mg, mmol) in 30 ml of CH₂Cl₂, Cu powder (272 mg) and triphenylbismuth diacetate (4.64 gm) were added. The reaction was stirred at room temperature overnight and progress was monitored subsequently by TLC. The crude reaction mixture was diluted with CH₂Cl₂ (20 ml), filtered, the filtrate washed with water and brine. The organic phase was dried over anhydrous Na₂SO₄; and solvent was removed under reduced pressure. The crude product was purified by column chromatography using EtOAc and hexane (1:9) as eluent to obtain a pail green solid (800 mg). ¹H NMR (CDCl₃): δ 6.0 (brs, NH), 7.05 (t, 1H, J=7.2 Hz), 7.15 (d, 2H, J=8.10 Hz), 7.35 (t, 2H, J=8.4 Hz), 7.45-7.55 (m, 2H), 7.60 (dd, 1H, J=1.8, 7.5 Hz), 7.70 (d, 1H, J=2.7 Hz), 8.00 (d, 1H, J=7.8 Hz), 8.70 (d, 1H, J=2.7 Hz).

Synthesis of 1-Methyl-3-phenylamino-quinolinium iodide

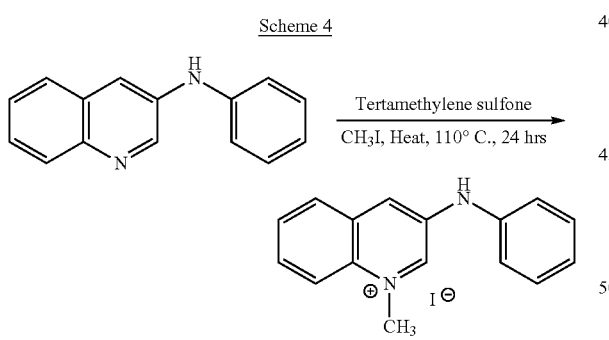

Scheme 4

A mixture of 3-anilinoquinoline (100 mg), methyl iodide (0.3 ml) and toluene (3 ml) in a sealed pressure tube was stirred at 110° C. for 24 hours. The reaction mixture was cooled to room temperature and diluted with Et₂O (15 ml) to precipitate the product. The product was filtered and washed with ether (3×20 ml) before purification by column chromatography using methanol as an eluent to yield the pure product as an orange solid (80 mg, mp: 182-183° C.). ¹H NMR (CD₃OD): δ 4.6 (s, 3H), 7.18 (m, 1H), 7.36 (dd, 2H, J=0.9, 7.5 Hz), 7.44 (m, 2H), 7.82 (t, 2H, J=6.0 Hz), 7.94 (m, 2H), 8.10 (d, 1H, J=8.4 Hz), 8.26 (d, 1H, J=8.6 Hz), 8.46 (d, 1H, J=2.4 Hz), 9.04 (d, 1H, J=2.7 Hz). Anal Calcd for: C₁₆H₁₅IN₂.1.3 H₂O: C, 46.98; H, 4.34; N, 6.85. Found: C, 46.81; H, 3.95; N, 6.54

Synthesis of (5-Bromo-pentyl)-cyclohexane: A mixture of 1,5-dibromopentane (16 gm, 69.97 mmol) in THF (20 ml) and a solution of (Li₂CuCl₄ in ether, 14 ml) under nitrogen at 5-10° C. was stirred for 25 minutes and then cyclohexyl magnesium bromide (10 gm, 69.97 mmol) was added dropwise over 30 minutes. The reaction was stirred at 0° C. for another 1 h, then at room temperature for 12 hr. The reaction mixture was cooled to 0° C., saturated with NH₄Cl solution (20 ml), diluted with ethyl acetate (100 ml) and the combined organic layer was separated, washed with brine and dried over anhydrous sodium sulfate. The solvent was removed under reduced pressure and the crude product was purified by column chromatography using hexane as an eluent. The pure product was an oily liquid (12.84 gm). ¹H NMR (CDCl₃): 0.8 (t, 2H, J=10.2 Hz), 1.00-1.38 (m, 9H), 1.52-168 (m, 6H), 1.70-1.80 (m, 2H), 3.38 (t, 2H, J=7.2 Hz).

Synthesis of (5-Iodo-pentyl)-cyclohexane: A mixture of (5-bromo-pentyl)-cyclohexane (2 gm, 8.58 mmol) in acetone (20 ml), and sodium iodide (2.57 g, 17.15 mmol) was heated at 60° C. for 12 hrs and then cooled to room temperature. The solvent was evaporated, the residue was taken up in EtOAc (30 ml), washed with water (20 ml) and then brine (30 ml). The organic layer was separated, dried over anhydrous sodium sulfate and solvent was removed under reduced pressure. The crude product was purified by column chromatography using hexane as an eluent to yield an oily liquid (1.36 gm). ¹H NMR (CDCl₃): δ 0.8 (t, 2H, J=10.2 Hz), 1.00-1.38 (m, 9H), 1.52-168 (m, 6H), 1.70-1.80 (m, 2H), 3.10 (t, 2H, J=6.9 Hz).

Synthesis of 1-(5-Cyclohexyl-pentyl)-3-phenyl-quinolinium iodide

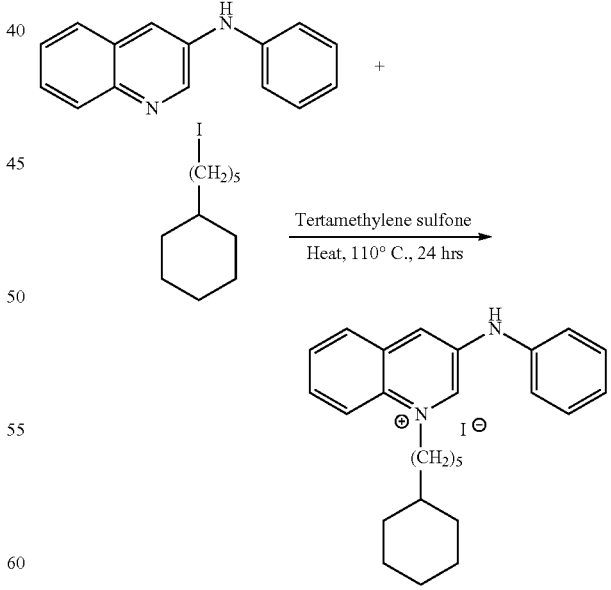

Scheme 5

A mixture of Phenyl-quinolin-3-yl-amine (100 mg, 0.45 mmol), toluene (3 ml), and 5-iodo-pentyl-cyclohexane (636 mg, 2.3 mmol) was sealed in a pressure tube and stirred at 110° C. for 24 hours. The reaction mixture was cooled to room temperature, diluted with Et₂O (15 ml) and the precipitated compound was filtered and washed with Et$_2$O (3×20 ml). The crude product was purified by column chromatography using methanol as an eluent to yield a pure product as an orange solid (65 mg, mp 156-158° C.). $^1$H NMR (CD$_3$OD): δ 0.80-1.00 (m, 2H), 1.00-1.38 (m, 7H), 1.40-1.58 (m, 4H), 1.60-1.80 (m, 4H), 2.00-2.20 (m, 2H), 5.00 (t, 2H, J=7.2 Hz), 7.20 (t, 1H, J=6.8 Hz), 7.35 (d, 2H, J=8.6 Hz), 7.46 (t, 2H, J=7.0 Hz), 7.80 (t, 1H, J=7.6 Hz), 7.82-8.00 (m, 1H), 8.10 (d, 1H, J=8.4 Hz), 8.38 (d, 1H, J=9.0 Hz), 8.45 (d, 1H, J=2.4 Hz), 9.0 (d, 1H, J=2.7 Hz). Anal Calcd for: C$_{26}$H$_{33}$IN$_2$.1.4 H$_2$O: C, 56.69; H, 6.55; N, 5.08. Found: C, 56.73; H, 6.26; N, 4.93.

Synthesis of 1-Phenyl-5-Iodo-pentane: A mixture of 5-phenyl-pentane-1-ol (1.0 gm, 6.089 mmol) in dichloromethane (20 ml), triphenyl phosphine (2.35 gm, 8.52 mmol), imidazole (0.58 gm, 8.52 mmol) and elemental iodine (2.16 gm, 8.52 mmol) was stirred at room temperature for 12 h and solvent was removed under reduced pressure. The crude mixture was taken up in ethyl acetate (30 ml), washed with water (20 ml) and then with brine (30 ml). The layers were separated, the organic layer was dried over anhydrous sodium sulfate and solvent was removed under reduced pressure. The crude product was purified on column chromatography using hexane as an eluent to yield an oily liquid, 750 mg. $^1$H NMR (CDCl$_3$): δ 1.30-1.70 (m, 4H), 1.80 (m, 2H), 2.6 (t, 2H, J=7.2 Hz), 3.10 (t, 2H, J=7.8 Hz), 7.00-7.34 (m, 5H).

Synthesis of 1-(5-Cyclohexyl-pentyl)-3-phenyl-quinolinium iodide

A solution of Phenyl-quinolin-3-yl-amine (100 mg, 0.45 mmol) toluene (2 ml) and 5-iodo-pentyl-benzene (373 mg, 1.36 mmol) in a sealed pressure tube was stirred at 110° C. for 24 hours. The reaction mixture was cooled to room temperature, diluted with Et$_2$O (15 ml) and the precipitated compound was filtered and washed with Et$_2$O (3×20 ml). The crude product was purified on a chromatographic column using methanol as an eluent to yield a pure product as an orange solid (75 mg, mp 140-141° C.). $^1$H NMR (CD$_3$OD): δ 1.42-1.56 (m, 2H), 1.66-178 (m, 2H), 2.04-2.18 (m, 2H), 2.58-2.68 (t, 2H, J=7.2 Hz), 4.88-5.04 (t, 2H, J=7.8 Hz), 7.08-7.24 (m, 6H), 7.14 (dd, 2H, J=0.9, 7.5 Hz), 7.40-7.44 (t, 2H, J=8.4 Hz), 7.76-7.84 (t, 1H, J=7.5 Hz), 7.86-7.94 (m, 1H), 8.08 (d, 1H, J=8.4 Hz), 8.30 (d, 1H, J=9.0 Hz), 8.46 (d, 1H, J=2.4 Hz), 9.04 (d, 1H, J=2.7 Hz). Anal Calcd for: C2$_6$H$_{27}$IN$_2$.1H$_2$O: C, 60.92; H, 5.70; N, 5.47. Found: C, 60.79; H, 5.33; N, 6.38.

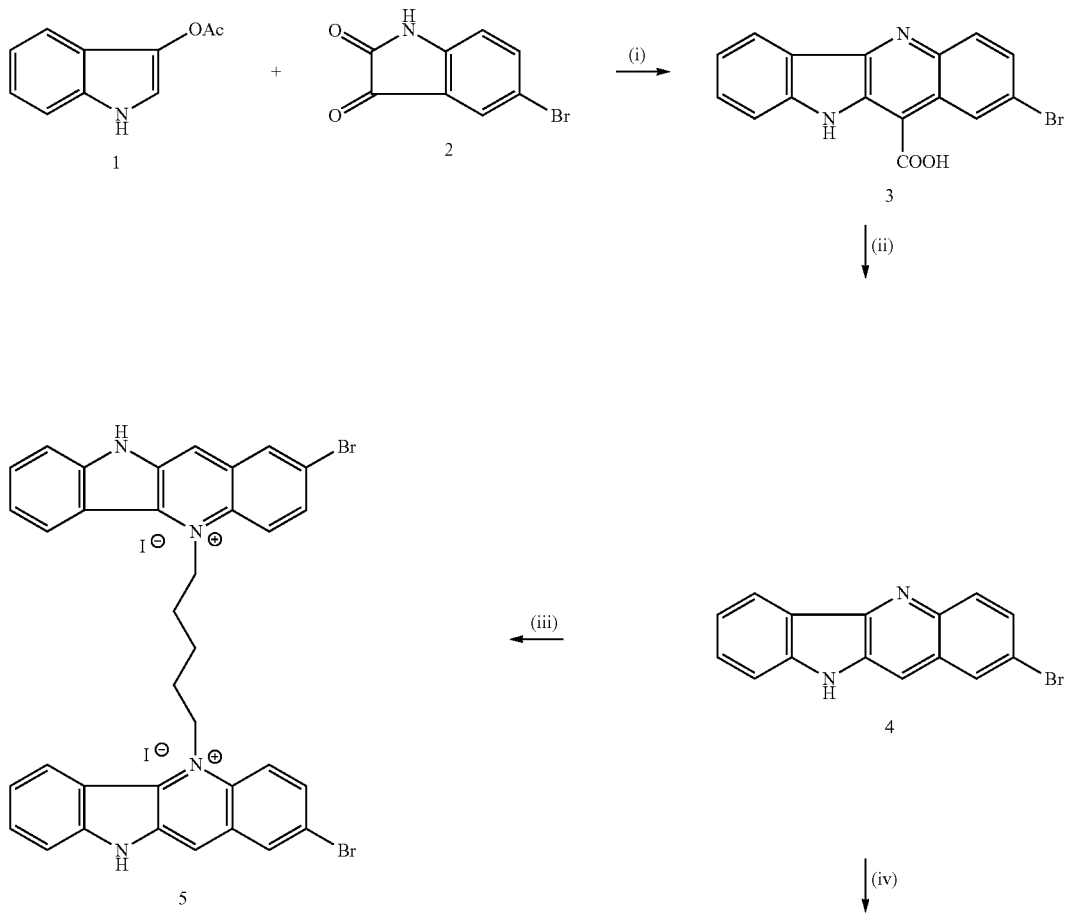

Scheme 6

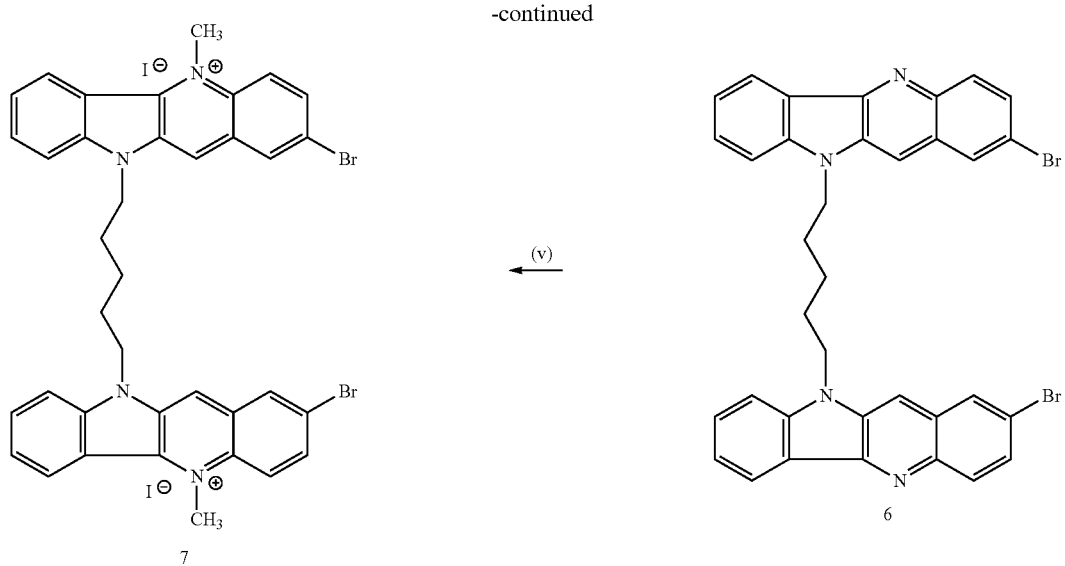

Reaction Conditions:
(i) Aqueous KOH, 10 days, (ii) Parafin Oil, 300° C., 4 hr. (iii) 1,5-Diiodoapentane, Tetramethylenesulfone, 110° C., 36 hr.
(iv) THF, NaH, 1,5-Dibromopentane, Reflux, 24 hr. (v) Methyliodide, Tetramethylenesulfone, 110° C., 36 hr.

Synthesis of 2-Bromo-1,5-bis(10-indole[3,2-b]quinolin-5-ium pentane)diiodide

A mixture of 2-bromo-10H-indole[3,2-b]quinoline (4) (300 mg, 0.67 mmol), 1,5-diiodopentane (160 mg, 0.40 mmol), and tetramethylene sulfone (3 mL) was sealed in a pressure tube and the solution was heated at 110° C. for 24 hrs. The mixture was allowed to cool to room temperature and diluted with $Et_2O$ (15 mL) to precipitate a yellow solid, which was collected by filtration. The solid was recrystallized form methanol-dichloromethane to give compound 5 (150 mg, mp 273-274° C.): $^1$H NMR (DMSO-$d^6$): δ 1.80 (m, 2H), 2.20 (m, 4H), 5.40 (m, 4H), 7.50 (t, 2H, J=8.1 Hz), 7.80 (d, 2H, J=8.1 Hz), 8.00 (t, 2H, J=7.5 Hz), 8.20 (dd, 2H, J=2.1, 7.5 Hz), 8.50 (d, 2H, J=8.7 Hz), 8.70 (d, 2H, J=9.6 Hz), 8.90 (d, 2H, J=2.1 Hz), 9.20 (s, 2H). Anal Calcd for: $C_{35}H_{28}Br_2I_2N_4 \cdot 4.5 H_2O$: C, 38.91; H, 3.45; N, 5.19. Found: C, 38.92; H, 2.71; N, 4.96.

Synthesis of 2-Bromo-1,5-bis(10-indolo[3,2-b]quinolin-10-yl)-pentane) (6)

To a mixture of 2-bromo-10H-indole[3,2-b]quinoline (4) (850 mg, 2.86 mmol) and NaH (242 mg, 6.06 mmol) dissolved in DME (15 ml) was added 1,5-diiodopentane (463 mg, 1.43 mmol) with stirring. After addition was completed, the reaction mixture was refluxed for 12 h at 0° C., allowed to cool to room temperature and DME was removed under reduced pressure. The residue is taken up in $Et_2OAc$ (20 ml), washed with water (20 ml) then with brine (20 ml) and dried over anhydrous sodium sulfate. The organic solvent was removed, and the crude product was purified by column chromatography to give a soft solid compound 6 (260 mg). $^1$H NMR (DMSO-$d^6$): δ 1.40 (m, 2H), 1.80-2.00 (m, 4H), 4.20-4.36 (m, 4H), 7.20-7.38 (m, 4H), 7.50-7.60 (m, 2H), 7.64 (s, 2H), 7.68 (d, 1H, J=2.4 Hz), 7.72 (d, 1H, J=1.8 Hz), 8.00 (d, 2H, J=2.1 Hz), 8.18-8.20 (d, 2H, J=9.0 Hz), 8.48-8.54 (d, 2H, J=7.8 Hz).

Synthesis of 2-Bromo-1,5-bis(10-indolo[3,2-b] quinolin-10-ium)pentane diiodide (7)

A mixture of bis-quindole, 6 (260 mg, 0.3925 mmol), methyl iodide (0.3 ml), and tetramethylene sulfone (2 mL) was sealed in a pressure tube and the solution was heated at 110° C. for 24 h and allowed to cool to room temperature. $Et_2O$ (15 ml) was added to produce a yellow precipitate which was subsequently recrystallized from methanol-dichloromethane to give the compound 7 (150 mg, mp: 258-259° C.). $^1$H NMR (DMSO-$d^6$): δ 1.40 (m, 2H), 1.80-2.00 (m, 4H), 5.00 (s, 6H), 7.44-7.54 (t, 2H, J=6.6 Hz), 7.82-7.94 (m, 4H), 8.20-8.26 (d, 2H, J=9.3 Hz), 8.56 (s, 2H), 8.70-8.74 (d, 2H, J=9.3 Hz), 8.76-8.82 (d, 2H, J=8.7 Hz), 9.36 (s, 2H). Anal Calcd for: $C_{37}H_{32}Br_2I_2N_4$: C, 46.96; H, 3.41; N, 5.92. Found: C, 47.12; H, 3.34; N, 5.82

Synthesis Compound 1:

A mixture of anthranilic acid (15 gm, mmol), dimethyl formamide (35 ml), and 1,4-dioxane (35 ml) was cooled to 0° C. in a round bottom flask and then bromoacetyl bromide (gm, mmol) was slowly added so that temperature did not rise above 1° C. At the end of the addition, the temperature was maintained at 0° C. for a further 15 min and then the mixture was stirred overnight at room temperature. The content of the flask was poured into water (400 ml), and the resulting precipitate 1 was filtered, washed with water (3×100 ml), and then dried to yield a colorless crystalline compound 1 (20 gm.). $^1$H NMR: ($CD_3OD$): δ 4.10 (s, 2H), 7.20 (dtd, 1H, J=1.2, 1.2 and 5.7 Hz), 7.54-7.60 (dtd, 1H, J=1.2, 1.5 and 5.7 Hz), 8.08-8.12 (dd, 1H, J=1.5, 6.3 Hz), 8.54-8.58 (dd, 1H, J=0.6, 7.8 Hz).

Scheme 7

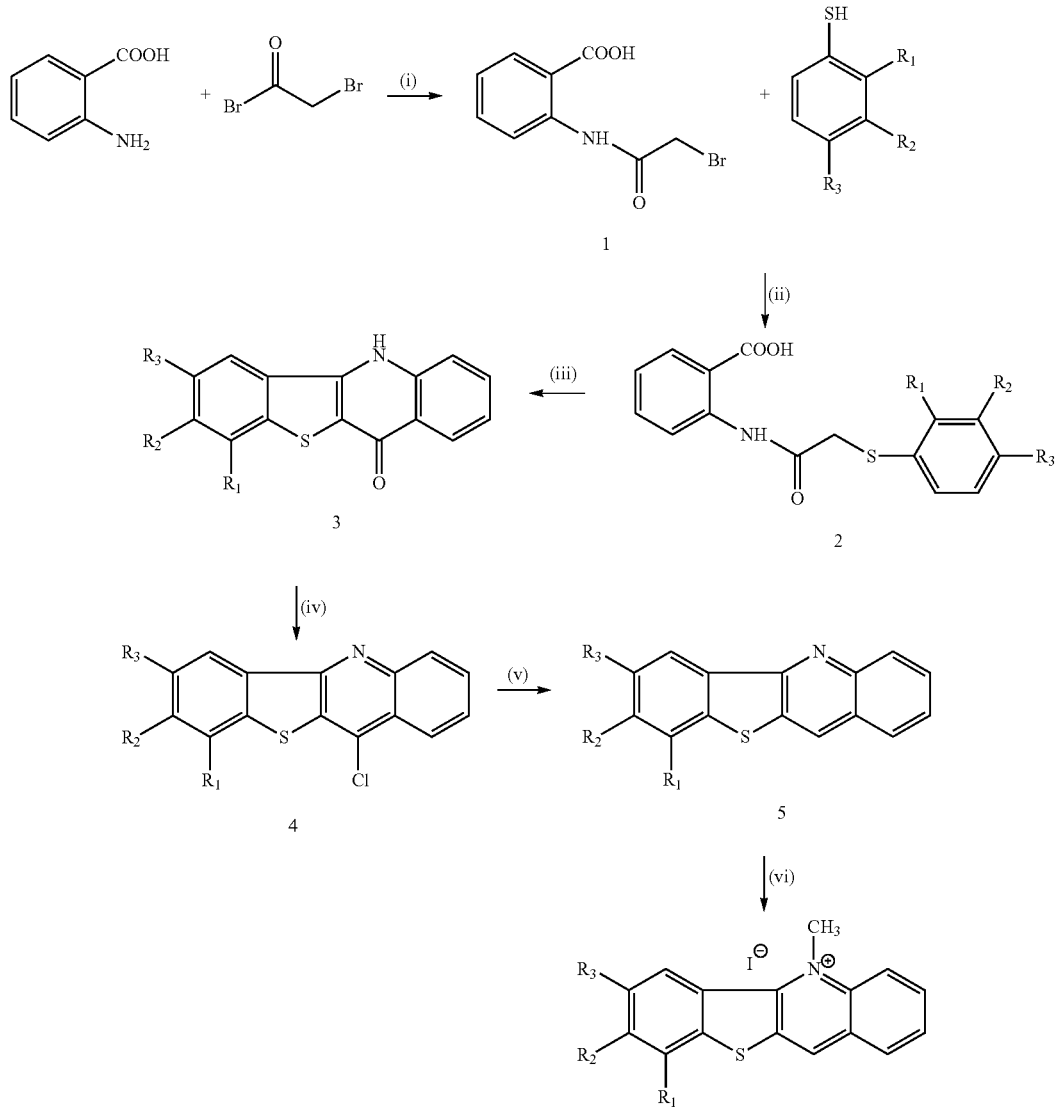

6a: $R_1 = Cl, R_2 = H, R_3 = H$
6b: $R_1 = H, R_2 = Cl, R_3 = H$
6c: $R_1 = H, R_2 = H, R_3 = Cl$

Reaction Conditions:
(i) DMF:1,4-Dioxane (1:1), RT, 24 hr. (ii) Acetone, $K_2CO_3$, KI, Refflux, 24 hr (iii) PPA, 130° C., 8 hr (iv) POCl3, 120° C., 6 hr.
(v) Pd/C/H$_2$, Ethylacetate, 8 hr (vi) Tetramethylenesulfone, 110° C., 48 hrs Compound 2a: A mixture of crude product 1 (10 gm, 38.75 mmol), 2-chlorobenzene-thiol (5.6 gm, 38.75 mmol), acetone (100 ml), $K_2CO_3$ (2.0 gm) and KI (200 mg) was refluxed for one day, cooled to room temperature and acetone was removed on a rotary vapor. The colorless precipitate was dissolved in water (200 ml) and 10% aqueous hydrochloric acid (100 ml) was added and solids were separated by filtration. The solid was washed with water (2×100 ml) and dried to give compound 2a as a colorless solid (8 gm). Compounds 2b and 2c were similarly prepared. $^1$H NMR: (CD$_3$OD): δ 3.90 (s, 2H), 7.00-7.08 (m, 1H), 7.12-7.18 (m, 1H), 7.20-7.23 (m, 1H), 7.30-7.32 (m, 1H), 7.33-7.40 (m, 1H), 7.46-7.52 (dd, 1H, J=1.5, 6.3 Hz), 8.00-8.04 (dd, 1H, J=1.5, 6.3 Hz), 8.38-8.44 (d, 1H, J=8.1 Hz). (2b) $^1$H NMR: (CD$_3$OD): δ 3.80 (s, 2H), 7.00-7.08 (m, 1H), 7.14-7.18 (m, 1H), 7.22-7.28 (t, 1H, J=7.8 Hz), 7.30-7.38 (m, 2H), 7.44 (t, 1H, J=2.1 Hz), 7.88-8.04 (dd, 1H, J=1.5, 6.0 Hz), 8.40-8.44 (dd, 1H, J=0.9, 7.5 Hz)). (2c) $^1$H NMR (CD$_3$OD): δ 3.90 (s, 2H), 7.10-7.16 (m, 1H), 7.24-7.30 (m, 2H), 7.38-7.44 (m, 7.48 (m, 1H), 8.02-8.04 (dd, 1H, J=1.5, 6.6 Hz), 8.50-8.56 (dd, 1H, J=0.9, 7.8 Hz).

Compound 3a: A mixture of crude 2-[2-(2-Chloro-phenyl-sulfanyl)acetylamino]-benzoic acid (8.0 gm), and PPA (120 gm) was stirred at 130° C. for 6 h, and then was poured onto ice/water (150 ml) and neutralized with aqueous sodium hydroxide solution until the pH=7. The solids were filtered and washed with water (2×100 ml), and dried. The crude product was used without further purification. Compounds 3b, 3c were similarly prepared.

(3b) $^1$H NMR: (DMSO-d$^6$): δ 7.32-7.34 (m, 1H), 7.60-7.64 (dd, 1H, J=2.1, 6.9 Hz), 7.70-7.80 (m, 2H), 8.18-8.24 (d, 1H, J=8.1 Hz), 8.26-8.28 (d, 1H, J=2.1 Hz), 8.48-8.54 (d, 1H, J=8.4 Hz), 12.80 (s, 1H).

Compound 4a:

A mixture of crude 3a (4 gm) and POCl$_3$ (30 ml) was stirred under reflux at 120° C. for 6 h. The reaction mixture was allowed to cool and then was poured onto ice/water (200 ml). The resulting mixture was neutralized with aqueous sodium hydroxide solution until the pH=7, the solid was filtered, washed with water (2×100 ml) and dried. The crude product was purified by column chromatography using ethyl acetate: hexanes (1:9) as eluent to yield a colorless solid (500 mg). Compounds 4b, 4c were similarly prepared.

$^1$H NMR: (CDCl$_3$): δ 7.52-7.58 (m, 1H), 7.62-7.68 (dd, 1H, J=0.9, 6.9 Hz), 7.70-7.76 (m, 1H), 7.82-7.88 (m, 1H), 8.30-8.38 (d, 2H, J=8.4 Hz), 8.54-8.60 (d, 1H, J=7.8 Hz). (4b) $^1$H NMR: (CDCl$_3$): δ 7.52-7.58 (dd, 1H, J=1.8, 6.6 Hz), 7.68-7.74 (m, 1H), 7.80-7.88 (m, 2H), 8.26-8.36 (m, 2H), 8.50-8.56 (d, 1H, J=8.4 Hz). (4c) $^1$H NMR: (CDCl$_3$): δ 7.58-7.62 (dd, 1H, J=2.1, 6.3 Hz), 7.68-7.74 (m, 1H), 7.76-7.88 (m, 2H), 8.26-8.38 (t, 2H, J=7.8 Hz), 8.60 (d, 1H, J=1.5 Hz).

Compound 5a:

A mixture of compound 4a (500 mg), in ethyl acetate (150 ml) and Pd/C (10%) (500 mg), was hydrogenated for 6 h. The reaction mixture was filtered through celite, washed with ethyl acetate (2×30 ml) and solvent was removed under reduced pressure. The pure product was obtained by column chromatography using ethyl acetate and hexanes to yield the desired compound 5a as a colorless solid (160 mg). Compounds 5b and 5c were similarly prepared. $^1$H NMR: (CDCl$_3$): δ 7.50-7.56 (t, 1H, J=7.5 Hz), 7.58-7.64 (m, 2H), 7.76-7.82 (m, 1H), 7.90-7.96 (d, 1H, J=8.4 Hz), 8.56-8.62 (d, 1H, J=7.8 Hz), 8.64 (s, 1H). (5b) $^1$H NMR: (CD$_3$OD): δ 7.52-7.56 (dd, 1H, J=1.8, 6.6 Hz), 7.58-7.64 (m, 1H), 7.74-7.82 (m, 1H), 7.90-7.94 (d, 1H, J=8.1 Hz), 8.26-8.30 (d, 1H, J=8.7 Hz), 8.56-8.58 (d, 1H, J=8.7 Hz), 8.60 (s, 1H). (5c) $^1$H NMR: (CD$_3$OD): δ7.58-7.70 (m, 2H), 7.76-7.86 (m, 2H), 7.92-7.98 (d, 1H, J=8.4 Hz), 8.44-8.50 (d, 1H, J=8.7 Hz), 8.68 (s, 1H), 8.86 (s, 1H).

Compound 6a:

A solution of 5a (150 mg) in tetramethylene sulfone (3 ml) and methyl iodide (0.3 ml) in a sealed tube was stirred at 110° C. for 36 hours. The reaction mixture was cooled to room temperature, diluted with diethyl ether (15 ml) to form a precipitate which was filtered and washed with ether (3×20 ml). The crude product purified by recrystallization using dichloromethane and methanol to yield the pure product as an orange solid (65 mg, mp 192-193° C.). Compound 6b (140 mg, mp: 218-219° C.) and 6c (130 mg, mp: 203-204° C.) were similarly prepared. $^1$H NMR: (CD$_3$OD): δ 5.20 (s, 3H), 7.88-7.94 (t, 1H, J=7.8 Hz), 8.04-8.14 (m, 2H), 8.34-8.42 (m, 1H), 8.50-8.54 (d, 1H, J=8.1 Hz), 8.78-8.80 (d, 1H, J=9.3 Hz), 9.02-9.04 (d, 1H, J=8.4 Hz), 9.88 (s, 1H). Anal Calcd for: C$_{16}$H$_{11}$ClINS.0.3CH$_3$OH: C, 45.24; H, 2.88; N, 3.23. Found: C, 44.90; H, 2.56; N, 3.22). (6b) $^1$H NMR: (CD$_3$OD): δ 5.20 (s, 3H), 7.86-7.94 (dd, 1H, J=1.8, 7.2 Hz), 8.04-8.10 (t, 1H, J=7.5 Hz), 8.30-8.40 (m, 1H), 8.44 (d, 1H, J=2.1 Hz), 8.48-8.52 (d, 1H, J=8.7 Hz), 8.72-8.80 (d, 1H, J=9.0 Hz), 9.00-9.06 (d, 1H, J=9.6 Hz), 9.80 (s, 1H). (6c) $^1$H NMR: (CD$_3$OD): δ 5.20 (s, 3H), 7.98-8.04 (dd, 1H, J=2.1, 6.6 Hz), 8.06-8.12 (t, 1H, J=7.8 Hz), 8.32-8.40 (m, 2H), 8.48-8.54 (d, 1H, J=8.4 Hz), 8.76-8.82 (d, 1H, J=9.0 Hz), 9.04 (d, 1H, J=1.5 Hz), 9.84 (s, 1H).

The invention claimed is:

1. A compound having the formula:

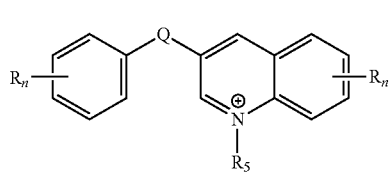

[IV]

wherein:

R is, -halogen, —CF$_3$, —O—R$_1$, —S—R$_1$, —S—R$_1$O, —S—R$_1$O$_2$, —CN, —NO$_2$, or —NR$_1$R$_2$, wherein R$_1$ and R$_2$ are the same or different and are alkyl or hydrocarbylaryl;

n is the position of substitution of R;

Q is Z or NH; and

Z is N—R$_{10}$, O, S, S=O, CH$_2$, or C=O with the proviso that where Z is NH, N—CH$_3$, S or O, and R$_n$ is H, R$_5$ may not be CH$_3$; and R$_5$ and R$_{10}$ are the same or different and are each independently a straight or branched C$_{1-5}$ chain substituted terminally by a cycloalkyl or aromatic ring.

2. The compound of claim 1, wherein the halogen is Cl, Br, F, or I.

3. The compound of claim 1, wherein R$_5$ is —CH$_3$; and Z is N—(CH$_2$)$_5$-Ph.

4. The compound of claim 1, wherein said compound is a quaternary salt.

5. The compound of claim 4, wherein said quaternary salt has the formula:

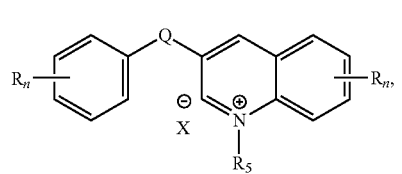

[VIII]

wherein: X is an anion, wherein X is I or tosylate.

6. A pharmaceutical composition comprising a pharmacologically effective amount of a compound of claim 1 and a pharmaceutically acceptable carrier.

7. The pharmaceutical composition of claim 6 comprising a pharmacologically antimycobacterial, antimalarial, or antifungal effective amount of the compound and a pharmaceutically acceptable carrier.

8. A method of treating a mammal in need of antimycobacterial, antimalarial, or antifungal-therapy comprising administering thereto a pharmacologically effective amount of a compound of claim 1.

9. An article of manufacture comprising packaging material and a pharmaceutical agent contained within said packaging material, wherein said pharmaceutical agent is effective for the treatment of a subject suffering from one or more of conditions of: a fungal infection, a mycobacterial infection, or malaria, and wherein said packaging material comprises a label which indicates that said pharmaceutical agent can be used for ameliorating the symptoms associated with said condition and wherein said pharmaceutical agent is a compound of claim 1.

* * * * *